(12) United States Patent
Verdonk et al.

(10) Patent No.: US 7,179,654 B2
(45) Date of Patent: Feb. 20, 2007

(54) BIOCHEMICAL ASSAY WITH PROGRAMMABLE ARRAY DETECTION

(75) Inventors: Edward Verdonk, San Jose, CA (US);
David Andrew King, Menlo Park, CA (US); Richard J. Pittaro, San Carlos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 734 days.

(21) Appl. No.: 10/100,346

(22) Filed: Mar. 18, 2002

(65) Prior Publication Data

US 2003/0175987 A1 Sep. 18, 2003

(51) Int. Cl.
G01N 21/76 (2006.01)
B32B 5/02 (2006.01)
B32B 27/12 (2006.01)
B32B 27/04 (2006.01)

(52) U.S. Cl. .............. 436/172; 422/82.05; 422/82.06; 422/82.07; 422/82.08; 422/82.09; 422/82.11

(58) Field of Classification Search ............... None
See application file for complete search history.

(56) References Cited

U.S. PATENT DOCUMENTS

| | | | |
|---|---|---|---|
| 5,157,262 A | 10/1992 | Marsoner et al. | |
| 5,455,178 A | 10/1995 | Fattinger | |
| 5,552,322 A | 9/1996 | Nemoto et al. | |
| 5,639,668 A | 6/1997 | Neel et al. | |
| 5,757,014 A | 5/1998 | Bruno et al. | |
| 5,779,978 A | 7/1998 | Hartmann et al. | |
| 5,812,272 A | 9/1998 | King et al. | |
| 5,936,261 A * | 8/1999 | Ma et al. ................ | 257/59 |
| 5,959,292 A | 9/1999 | Duveneck et al. | |
| 6,018,187 A | 1/2000 | Theil et al. | |
| 6,039,925 A | 3/2000 | Nemoto | |
| 6,066,243 A | 5/2000 | Anderson et al. | |
| 6,078,705 A | 6/2000 | Neuschafer et al. | |
| 6,083,763 A * | 7/2000 | Balch ..................... | 436/518 |
| 6,084,683 A | 7/2000 | Bruno et al. | |
| 6,110,749 A | 8/2000 | Obremski et al. | |
| 6,331,438 B1 * | 12/2001 | Aylott et al. ............ | 436/172 |
| 6,784,982 B1 * | 8/2004 | Blumenfeld et al. ..... | 356/71 |
| 2004/0027462 A1 * | 2/2004 | Hing ....................... | 348/222.1 |

* cited by examiner

Primary Examiner—Jill Warden

(57) ABSTRACT

A biochemical sensor apparatus having an optical radiation source, a sensor array, and a photodetector array is disclosed. Each sensor of the sensor array includes fluorophores for fluorescence (generating response radiation) when mixed with analytes of interest and exposed to stimulus radiation. An array of photodetectors, such as a CMOS imaging array is used to detect the response radiation. The detected response radiation is converted to digital values and the digital values used to analyze various properties of the analytes present in the sensors.

12 Claims, 5 Drawing Sheets

US 7,179,654 B2

BIOCHEMICAL ASSAY WITH PROGRAMMABLE ARRAY DETECTION

BACKGROUND

The present invention relates to the art of detection and analysis of analytes using fluorescence. More particularly, the present invention relates to detection of optical signals from multiple biochemical sensors using a photo detection array.

Fluorescence-based biochemical sensors are used to measure many analytes of physiologic interest. For example, fluorescence-based blood analyzers that measure blood gases, electrolytes, metabolites, coagulation state, and immunological markers are commercially available. The ability to measure multiple analytes in parallel is generally useful for the diagnosis of a patient's state of health. This requires an array of biochemical sensors (biosensors) and optical devices to detect the fluorescence from the samples.

Light from an array of biosensors is typically measured using one of the following devices and techniques: dedicated photodetectors, one discrete detector per sensor; a single photodetector, like a photomultiplier, and a scanning light collection system; or a multielement CCD (charge-coupled device) detector. All three approaches have their limitations.

Using one discrete detector per biosensor is costly because each biosensor typically requires a detector, amplifier, and an A/D (analog-to-digital) converter. Therefore, the number and the cost of the components grow proportionally to the number of the biosensors in the array. As the number of components grows, power requirement is increased, system reliability is decreased, and bulk is increased. Using a single detector in combination with a scanning light collection system is mechanically complex and not easily miniaturizable. Using a multielement CCD detector leaves little flexibility in readout of data because the individual elements of the array are not randomly addressable. This may limit the ability to measure signals changing rapidly in time. Further, CCD's suffer from the additional limitation of image blooming, where a saturated pixel leads to charge spill over on adjacent pixels.

Accordingly, there is a need for a technique and an apparatus overcoming these shortcomings of the current art.

SUMMARY

The need is met by the present invention. According to a first aspect of the present invention, a method of assaying analytes in a sample is disclosed. First, stimulus radiation is applied to a sensor having the analytes and fluorophores, the applied radiation causing the fluorophores to fluoresce generating response radiation. Then, the response radiation is filtered from the sensor, the sensor associated with at least one filter. Next, the response radiation is imaged onto a photodetector array where each photodetector of the photodetector array is smaller than the image. The photodetector array has at least a first subset of photodetectors and a second subset of photodetectors. The photodetector array converts the response radiation into digital values. The intensity of the imaged response radiation is determined for each subset of photodetectors. In addition, the intensity of the first subset of photodetectors is calibrated using the intensity of the second subset of photodetectors. The calibration is performed by subtracting weighted values of the intensity of the first subset of photodetectors from values of the intensity of the second subset of values.

In a second aspect of the invention, a method of assaying analytes is disclosed. First stimulus radiation is applied to a sensor having the analytes and fluorophores, the applied radiation causing the fluorophores to fluoresce generating response radiation. Then, the response radiation is filtered from the sensor, the sensor associated with at least two polarization filters. Next, the response radiation is imaged onto a photodetector array where each photodetector of the photodetector array is smaller than the image. The photodetector array has a first subset of photodetectors and a second subset of photodetectors. The photodetector array converts the response radiation into digital values. The intensity of the imaged response radiation is determined for each subset of photodetectors. In addition, the intensity of the first subset of photodetectors is calibrated using the intensity of the second subset of photodetectors. Finally, fluorescence lifetime characteristic is determined.

In a third aspect of the invention, a method of assaying analytes in a sample is disclosed. First, stimulus radiation is applied to a sensor having the analytes and fluorophores, the applied radiation causing the fluorophores to fluoresce generating response radiation. The response radiation is filtered. Then, the response radiation is imaged onto a photodetector array where each photodetector of the photodetector array is smaller than the image. The photodetector array has a first subset of photodetectors and a second subset of photodetectors. The photodetector array converts the response radiation into digital values. Next, intensity of the imaged response radiation is determined for each subset of photodetectors. Finally, the intensity of the first subset of photodetectors is calibrated using the intensity of the second subset of photodetectors.

In a fourth aspect of the invention, an apparatus is disclosed. The apparatus includes a sensor including fluorophores for generating response radiation in reaction to stimulus radiation when analyte is present within the sensor. Further, the apparatus includes a set of detectors for detecting the response radiation from the sensor. The sensor is one sensor in a plurality of sensors, each sensor of the plurality of sensors associated with a unique set of detectors.

In a fifth aspect of the invention, an apparatus is disclosed. The apparatus includes a radiation source for generating stimulus radiation and light pipe illuminator for directing the stimulus radiation to a sensor array. The sensor array includes an array of sensors. Each sensor has fluorophores for generating response radiation in response to the stimulus radiation when analyte is present within the sensor. The apparatus further includes a detector array for detecting the response radiation. The detector array includes a plurality of detectors grouped in sets, each set associated with a single sensor.

Other aspects and advantages of the present invention will become apparent from the following detailed description, taken in combination with the accompanying drawings, illustrating by way of example the principles of the invention.

DETAILED DESCRIPTION

Figure 1:
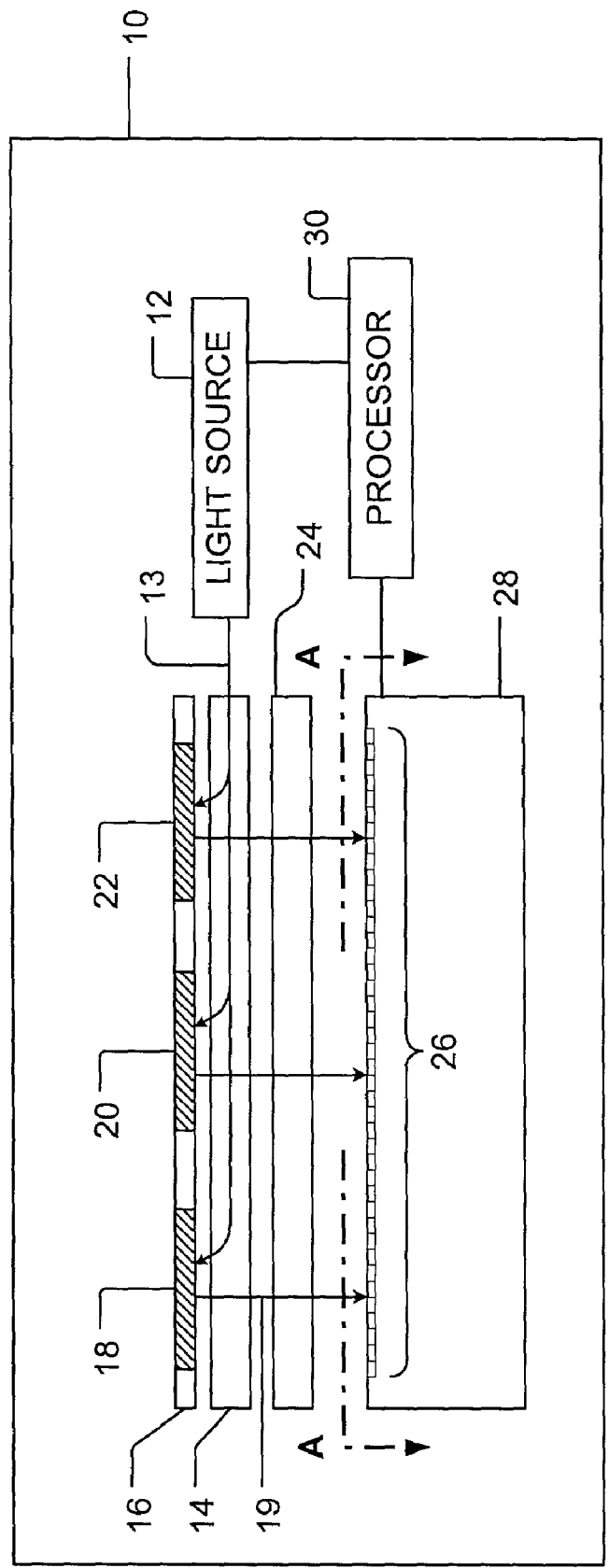
FIG. 1 is a simplified diagram of an optical apparatus according to one embodiment of the present invention.

As shown in the drawings for purposes of illustration, the present invention is embodied in an apparatus that produces stimulus optical radiation, directs that radiation to a fluorescence-based biosensor that generates response radiation in reaction to stimulus radiation when the analyte of interest is present within the biosensor, and reads the response radiation with an array of photodetectors differentially responsive to the response radiation. This configuration can take advantage of CMOS detector arrays that are readily obtainable in the marketplace. Using these detector arrays, the present inventive configuration is cost effective, technologically advantageous, and provides capabilities in fluorescence measurements that were not available using the traditional configurations and methods.

The cost of CMOS detector arrays, or imaging arrays, is declining as supply increases driven by demand in various imaging technologies. A CMOS imaging array has multiple photodetectors operating in parallel, allowing multiple fluorescent spots to be read by a single array without the need for mechanical scanning. Unlike a CCD, its photodetectors are randomly addressable, offering much more flexible control over where and when optical signals are measured. In addition, a CMOS array does not suffer from image blooming. Further, the CMOS imaging array is often fabricated with amplifiers and A/D converters, thereby eliminating the need for separate amplifiers and A/D converters for each detector.

Referring to FIG. 1, a biochemical assay apparatus 10 includes an optical radiation source 12 for generating stimulus radiation 13. For example, the radiation source 12 may be an LED (light emitting diode) 12 generating blue light 13. The light 13 is directed by a light pipe illuminator 14 to a biosensor array 16 including an array of biosensors 18, 20, and 22. Operation of the apparatus 10 is discussed using a flowchart of FIG. 2.

Figure 2:
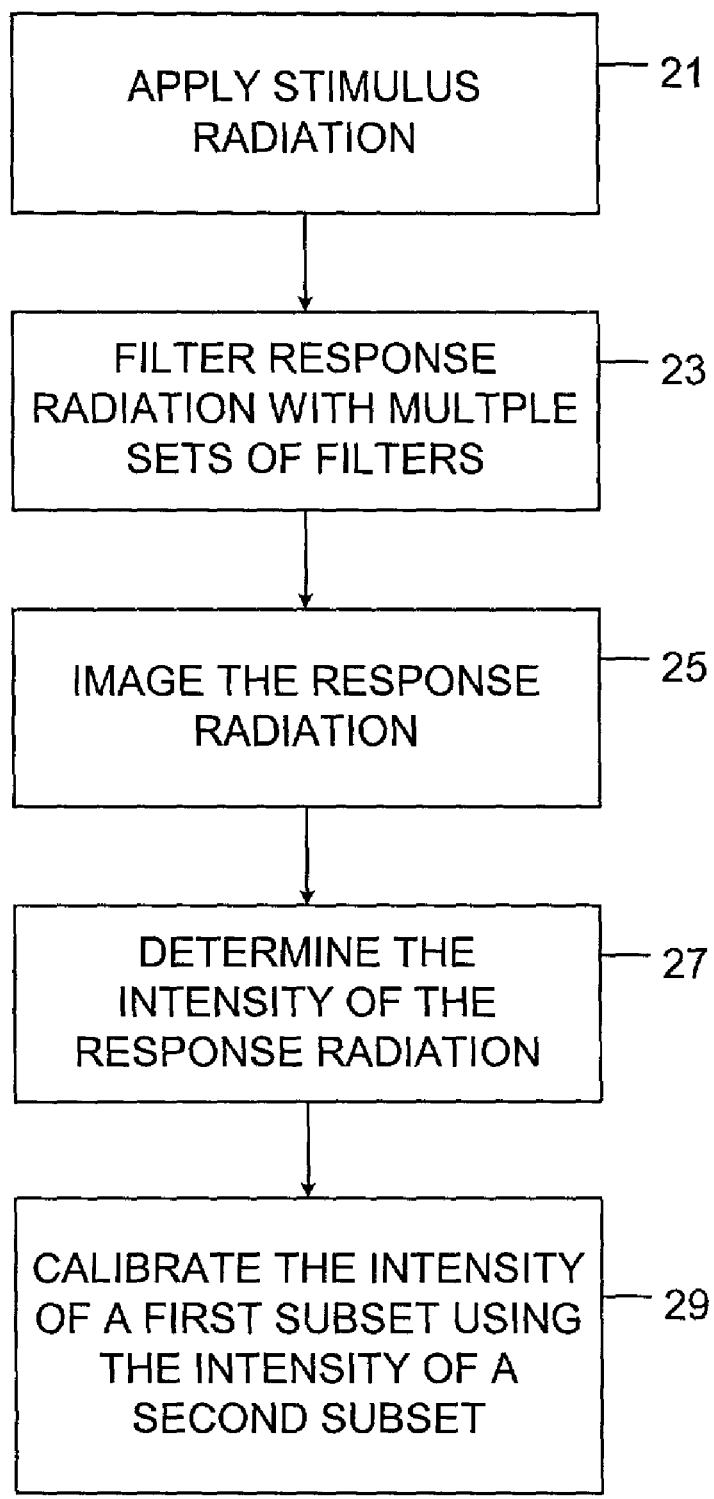
FIG. 2 is a flowchart illustrating one embodiment of the present invention.

Referring to FIGS. 1 and 2, each biosensor, for example biosensor 18, includes fluorophores that, when analytes of interest are present within the biosensor, cause the sensor to fluoresce when stimulated by application (step 21) of the stimulus radiation 13. For example, the biosensor 18 may include a ruthenium compound as the fluorescent species. When blood is introduced to the biosensor 18 and the blue light 13 impinges upon the biosensor 18, the fluorophores of the biosensor 18 generate red light 19 as response radiation 19 in response to the stimulus radiation 13. Arrows 13 and 19 of FIG. 1 are used for generally indicating the direction of the radiation (light) and are not intended to depict ray traces.

The response radiation 19 passes through the light pipe illuminator 14, through optical filters 24 which may include one or more sets of color filters or a set of polarizing filters, and is imaged onto a multiplicity of photodetectors within a detector array 26. The filtering step is illustrated by procedural step 23 of FIG. 2. The color optical filters can be used for determining color distribution of the response radiation 19. The polarizing filters can be used to determine polarization of the response radiation 19, relative to the polarization state of the stimulus radiation 13. The imaging step is represented by procedural box 25 of FIG. 2. In one embodiement, it is accomplished by an array of microlenses built into the lightpipe illuminator. In an alternative embodiment a separate microlens array, such as an array of gradient index lens is placed between the lightpipe illuminator 14 and the detector array 26. The detector array 26 includes a plurality of detectors, each detector referred to as a pixel on the array. In one embodiment, the detector array 26 has 307,200 pixels in a rectangular array having 640 pixels on one side and by 480 pixels on the orthogonal side. The detector array 26 may be fabricated on a detector unit 28. Further, the detector unit 28 may also incorporate amplifiers and A/D converters for converting the detected response radiation to digital values. The detector unit 28 may be, for example, a CMOS imaging array such as available from Agilent Technologies, Inc. as part number HDCS-2020. The detected radiation is converted into digital values by the CMOS detector unit 28 and provided to the processor 30 for analysis. The detector array 26 is an array of photodetectors. Here, for the purposes of describing the present invention, terms "photodetectors" and "detectors" are used interchangeably.

Figure 3A:
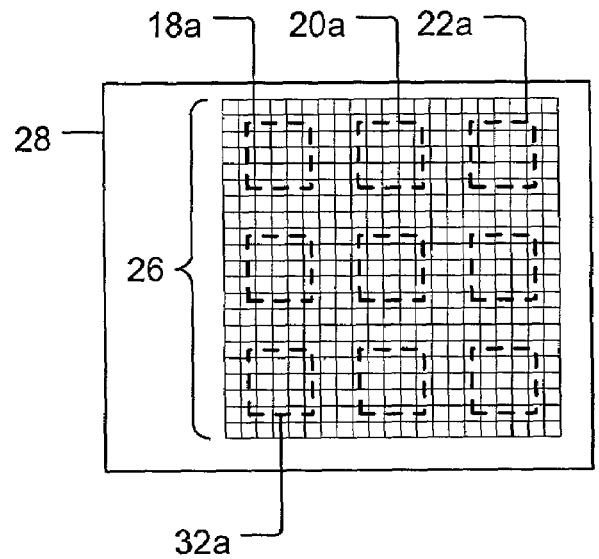
FIGS. 3A and 3B illustrate a fluorescence detector apparatus in accordance with one embodiment of the present invention.

FIG. 3A illustrates the apparatus 10 of FIG. 1 as viewed from line A—A of FIG. 1, illustrating in more detail the fluorescence detector unit 28 including the detector array 26. Referring to FIGS. 1 and 3A, the response radiation 19 is imaged on the photodetector array 26 having sets of photodetectors 18a, 20a, and 22a are associated with the sensors 18, 20, and 22, respectively. For example, the response radiation 19 from the biosensor 18 is detected by the set 18a of detectors. Here, each photodetector, or pixel, of the detector array 26 can be about ten microns by ten microns in size. The biosensor array 16 may include other biosensors not shown in FIG. 1 but each biosensor of the biosensor array is associated with a unique set of detectors, each unique set being a portion of the detector array 26. For example, the biosensor array 16 may include biosensor 32 (not shown) associated with set 32a of detectors.

In one embodiment of the present invention, light and its intensity from each biosensor are detected and measured by one or more detectors or sets of detectors of the detector array 26. See procedural box 27 of FIG. 2. Further, each pixel is substantially smaller than the image of the biosensor they are measuring so that redundancy can be used to relax alignment constraints. That is, a misalignment of the image of a given biosensor on the detector array 26 necessitates adjusting which pixels reads the biosensor; however this does not mean the loss of light that could be experienced for a similar misalignment when using a single photodetector.

Figure 3B:
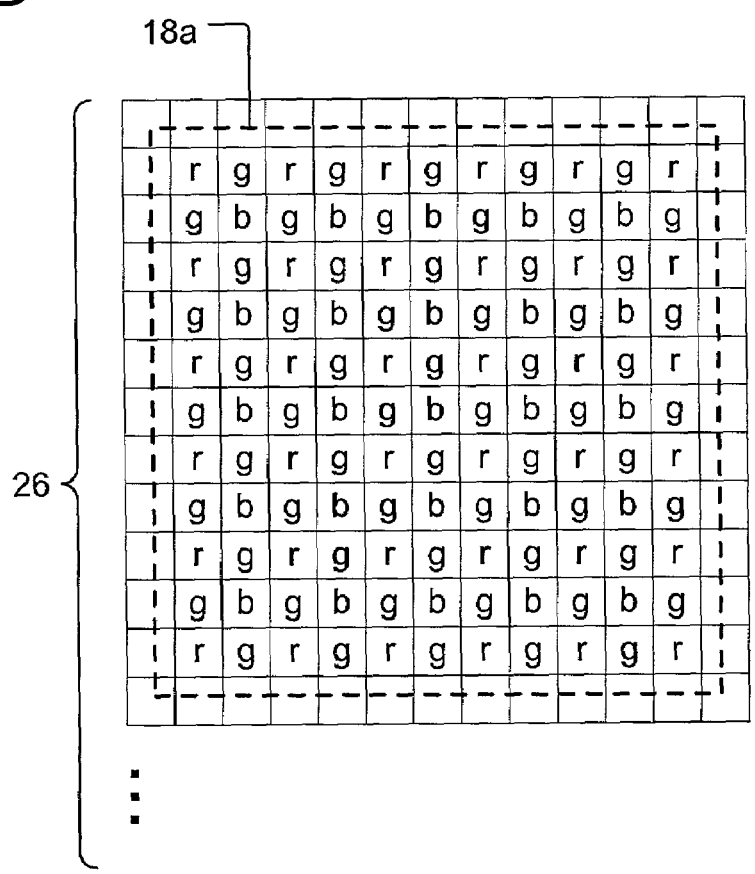

FIG. 3B illustrates one example of this redundancy. In the illustrated embodiment, the optical color filters are built into each pixel of the detector array 26. The regularity of the filter pattern means that the image of biosensor 18 can be shifted laterally on the detector array 26 by one or more rows or columns without affecting the measurement, provided that the image covers enough cycles of the filter pattern.

Figure 3C:
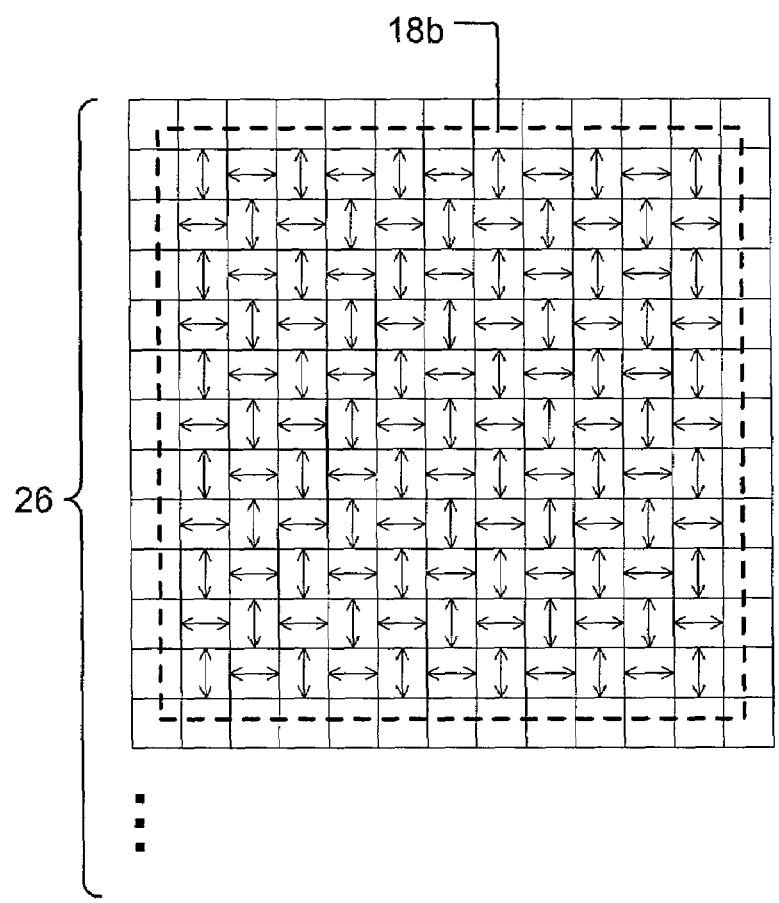
FIG. 3C illustrates a fluorescence detector apparatus in accordance with an alternate embodiment of the present invention.

Other types of filters, either built into the pixels themselves or placed like component 24 of FIG. 1, can be used to extend this concept. FIG. 3C illustrates a second embodiment where optical polarization filters, at two orthogonal orientations, have been incorporated into each pixel of the detector array 26 to determine the polarization or anisotropy of the response radiation.

The choice of type, number, and placement of optical filters relative to the sets of photodetectors of the detector array 26 will depend on what biosensors are being interrogated and what types of fluorescent measurements are being made. For instance, the intensity at one wavelength, the intensity ratio for two wavelengths, the color distribution of the intensity, the lifetime, the polarization, and other measurements of the response radiation 19 can all be determined, possibly all simultaneously on the same array of biosensors 16. Once the response radiation 19 is detected and converted to digital values, methods of determining the listed measurements are known in the art. Benefits of this arrangement are made clear in the following illustrative examples.

EXAMPLE 1

Basic Fluorescence Intensity Measurements

The operations of the assay apparatus 10 can be explained using the following example. Continuing to refer to FIGS. 1, 3A, and 3B, to measure fluorescence intensity of fluorophores (when exposed to analytes in a sample of blood), the blood sample is introduced to the biosensor array 16. In one embodiment, the size of each biosensor of the biosensor array 16 is 100 to 1000 microns in each lateral dimension and about 100 microns thick. One biosensor, for example, biosensor 18, contains ruthenium-based dye as the fluorophore to detect oxygen ($O_2$) in the blood sample, while the other biosensors 20 and 22 of the biosensor array 16 may contain other fluorophores to measure other blood analytes of interest, for example, sodium (Na), potassium (K), or pH.

The stimulus radiation 13 from the radiation source 12 is directed to the biosensors 18, 20, 22 of the biosensor array 16. The fluorophores (ruthenium in biosensor 18), reacting with the analytes of the blood sample, fluoresce generating response radiation 19 that is generally red for ruthenium.

FIG. 3B illustrates the set 18a of detectors associated with biosensor 18. The set 18a is preferably a portion of a CMOS imaging array and is a part of a detector unit 28 including an amplifier and A/D (analog to digital) circuitry for converting the response radiation 19 to digital values. The digital values are communicated to a processor 30 of FIG. 1 for analyzing the digital values.

In the sample embodiment illustrated in FIG. 3B, the set 18a includes 121 detectors, or pixels, arranged in an 11 pixel by 11 pixel rectangle. Some of the pixels (first subset) of the set 18a detect light at a first range of wavelengths (color band) for example, red light, and the other pixels (second subset) of the set 18a detect light at a second range of wavelengths (color band) for example green. In fact, in the illustrated embodiment, the set 18a of the detectors are mosaic'ed detectors of three primary colors—red, green, and blue—and these detectors are depicted using squares having, respectively, "r," "g," and "b" letter designations. In practice, optical filters optimized for specific fluorophores would be used in place of the generic "r", "g", and "b" filters used here for purpose of illustration. The subsets may be grouped by the detector type or by adjacency.

The response radiation 19 is detected by the detectors 26 and converted into digital values, or digitized. One benefit of this approach is that the registration requirements of the biosensor with its detector set are simplified. Specifically, in the present example, the red subset of the set 18a of detectors detects the response radiation 19 from the biosensor 18, however the red subset of set 20a or set 22a could serve equally well. This gives a great deal of flexibility to the biochemical assay apparatus 10.

A second benefit to this approach of using multiple subsets of pixels is that the intensity of the first subset can be calibrated using the intensity of the second subset. This step is represented by procedural box 29 of FIG. 2. For example, referring again to FIG. 3B, suppose the pixels 18a are detecting red emission light from a ruthenium-based biosensor that is being excited to fluoresce using blue excitation light. Then, a weighted average of the digitized values from the blue sensitive pixels, those labeled "b", can be used to detect the amount of scattered excitation light, an undesirable complication when measuring fluorescent light. This value can be subtracted from the average of the digitized value from the red sensitive pixels, those labeled "r", which are detecting fluorescent emission light, but perhaps some blue light as well. The weighting factor applied to the average of the digitized values would take into account the spectral characteristics of the optical radiation source and of the color filters as well as the spectral characteristics of the photodetectors quantum efficiency.

In another embodiment, a second subset of pixels would have associated with them a set of neutral density filters rather then color filters. Each neutral density filter can have a uniform transmission versus wavelength behavior to assure equal passage of light at all excitation wavelengths. One could then, easily and intentionally, scatter or reflect excitation light to this second subset of pixels to an extent that the intensity of the excitation light completely overwhelms the intensity of any fluorescent emission light. In this manner, the intensity of the excitation light source can be monitored and any fluctuations so determined can be used to correct the intensity of the fluorescent emission that is being simultaneously measured using a first subset of pixels.

EXAMPLE 2

Fluorescence Intensity Measurements with Referencing

The biosensor 18 may include two or more types of fluorophores. For example, the biosensor 18 may include a first fluorophore for reacting with a particular analyte to generate a first band of light when the stimulus 13 is introduced and a second fluorophore (a reference, or calibrating, fluorophore) to generate a second band of light when the stimulus 13 is introduced. Both the first band and the second band of light are components of the response radiation 19. The second band of light can be used for calibrating of the digital value of the response radiation 19 or for removing interferences. For example a green fluorescent fluorophore, designed to measure pH, may be mixed together with a red fluorescent fluorophore designed to measure dissolved oxygen. The red subset of detectors 18a shown in FIG. 3B would detect primarily the oxygen response of the biosensor and the green subset of detectors 18a would detect primarily the pH response of the biosensor. Then, a known pH interference of the oxygen sensor could be corrected for in software. Indeed, the biosensor 18 may include multiple fluorophores for testing different aspects of the same analyte, different analytes, or both. In either case, the response radiation 19 would include several color bands. One benefit of this arrangement is that different fluorophores in the biosensor are exposed to the same environmental conditions like temperature or excitation light intensity that also affect fluorescence intensity. Alternatively, material for the reference fluorophore can be selected that is unaffected by the analyte the sensor 18 is designed to measure.

EXAMPLE 3

Fluorescence Lifetime Measurements

Another use of the digital values is to determine the fluorescence lifetime characteristics curve of the fluorophore in the presence of an analyte of interest (FIG. 3). When the stimulus radiation 13 impinges the biosensor 18 containing the analyte and fluorophores, the fluorophores generate response radiation 19, for example, red light. The amount of the response radiation 19 generated decays over a period of time. The decay time may range from several nanoseconds to several microseconds. For example, ruthenium compounds can have lifetimes in the range of one microsecond in the absence of oxygen, to perhaps ten nanoseconds in a 100% oxygen environment.

The fluorescent lifetime can be measured by time sampling the fluorescence decay (time-domain measurement) or by measurement of the phase in a synchronously demodulated detector (frequency-domain measurement) as known to those skilled in the art.

Figure 4:
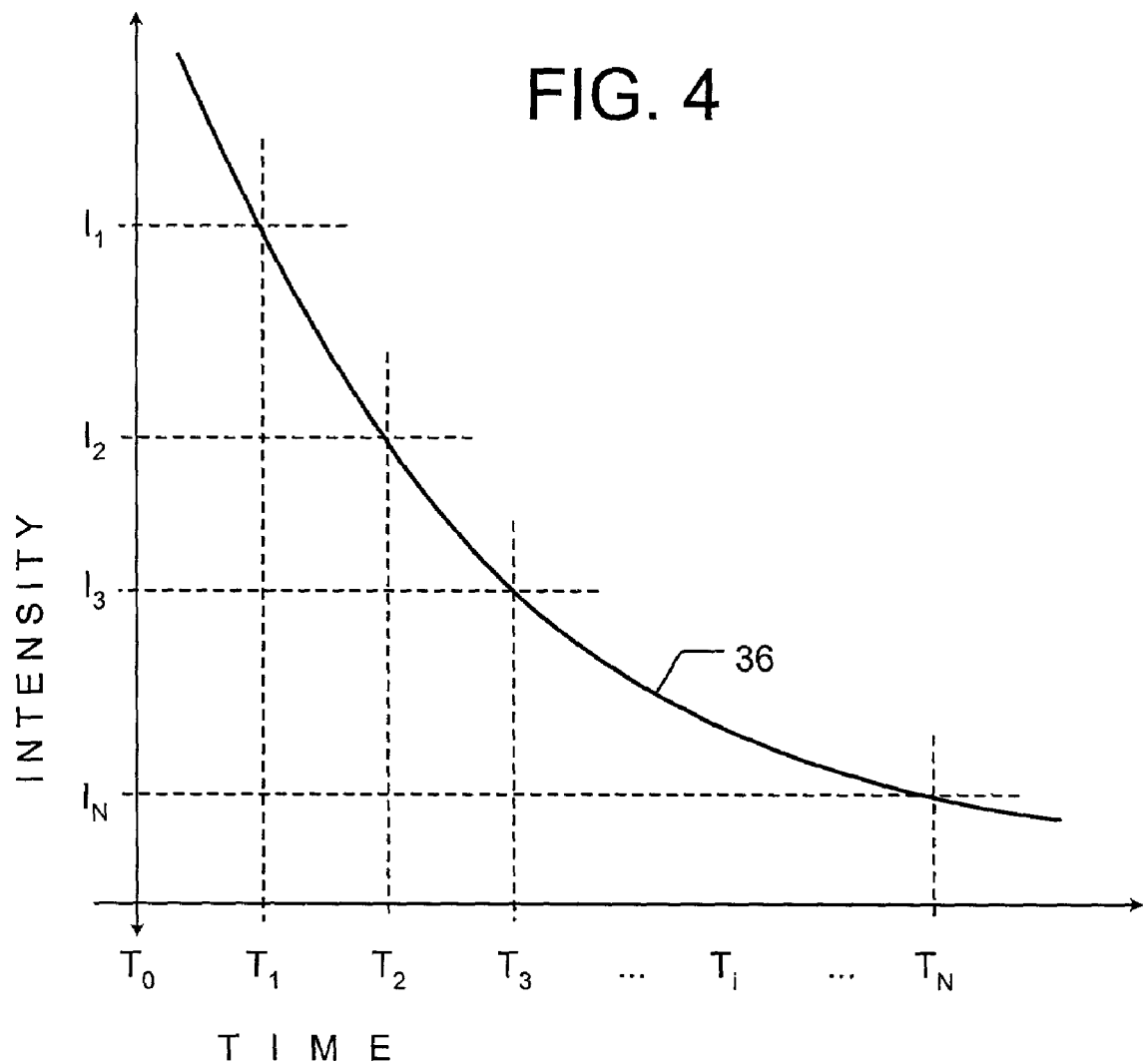
FIG. 4 is a sample fluorescence lifetime curve.

In one embodiment, time sampling of the fluorescent decay of a relatively long-lived fluorophore is possible using the pixel clock of the detector array. It would synchronize the modulation of the excitation light source with the timing signals—the reset, integrate, sample and read sequence—it supplies to each of the pixels being read. More specifically, if a biosensor 18 of the biosensor array 16 is homogeneous in construction and uniformly illuminated with the stimulus radiation 13, then each of the pixels 18a of the detector array 26 should detect equivalent emission light intensity if sampled at the same time. Rather than integrating and reading all the pixels 18a at the same time, one could time stagger their usage with respect to the stimulus 13, and thereby construct the illustrated curve 36 of FIG. 4.

To determine the shape of the curve 36, the biosensor 18 is exposed to the stimulus 13 at time $T_0$. At time $T_1$, some subset of pixels 18a are read to determine the intensity, $I_1$, of the fluorescence. At time $T_2$, some other subset of pixels 18a are read to determine the intensity, $I_2$, of the fluorescence, and so on. This is repeated until time at which time the final intensity $I_N$ is read. Thus, using this time staggering method of reading the subsets of pixels 18a at different times, the intensity of the response radiation 19 is found. A subset of pixels 18a may be a few as one, depending on the programming flexibility of the photodetector array. The interval of time between the sample times, for example between times $T_1$ and $T_2$ is arbitrary and depends upon various factors such as the analyte being analyzed, fluorophores used, etc. With the timing and the intensity information, the curve 36 is easily determined using known curve-fitting techniques.

The measurement of fluorescent intensity as a function of time by time sampling different subsets of pixels is possible because each of the pixels of the detector array 26, thus each set of the pixels of the array 26, are independently addressable. To synchronize the measurements following the stimulus 13, the light source 12 can be connected to the processor 30 for the processor 30 to control the firing of the light source 12 to provide the stimulus 13 to the sensor array 16 at time $T_0$.

An alternative method for obtaining the lifetime curve 36 of the response radiation is to use only one detector subset,—, but to expose that subset to multiple stimulus 13—read cycles. After each exposure, the intensity of the response radiation 19 is read using the chosen subset of detectors of the set 18a, and the delay time between next stimulus and its read incremented prior to application of the next excitation stimulus. That is, after the first exposure (at time $T_0$), the subset of pixels 18a are read at time $T_1$ following the first exposure; after the second exposure (again at time $T_0$), the subset of pixels 18a are read at time $T_2$ following the second exposure; and so on until N measurements of intensity are taken.

In yet another embodiment, the excitation source is modulated continuously rather than pulsed and the detector set devoted to each biosensor is subdivided into two subsets that monitor the response radiation at different times to derive its in-phase and quadrature components, and therefore its phase relative to the stimulus radiation. This phase can be used to calculate the fluorescent lifetime as known to one skilled in the art.

EXAMPLE 4

Fluorescence Lifetime Measurements with Referencing

Two different fluorophores, each fluorescing with a different color, are incorporated into the same biosensor and the lifetimes of the two fluorophores are measured independently with separate detector subsets and overlying color filters. The lifetime of one of the fluorophores is used as a reference for the second fluorophore.

EXAMPLE 5

Fluorescence Lifetime Measurements via Polarization

Fluorescent lifetimes of species whose lifetimes are short and that experience dynamic quenching can be measured using steady-state fluorescent polarization as taught by Zuckerman in U.S. Pat. No. 5,626,134. The basic idea is to match the rotational relaxation of the fluorophore to its decay time in the presence of a quencher. Then, as the concentration of quencher is decreased, the fluorescent lifetime of the fluorophore increases and is manifested as a change in the polarization or the anisotropy of the fluorescent light. A detector array 26 that incorporates polarization filters on its pixels, as shown in one embodiment in FIG. 3C, would be capable of monitoring an array of biosensors 16 using the method described. In FIG. 3C, an alternative embodiment of the photodetector array 26 including a set 18b of photodetectors incorporating polarization filters is illustrated.

FIGS. 3B and 3C show each pixel of the photodetector with its own optical filter, as might be expected if the filters are included during manufacture of the detector array. An alternative embodiment, illustrated by component 24 of FIG. 1, uses larger filters shared among more than one pixel and put in place after manufacture of the detector array. For example, a pair of polarizing filters, orthogonally oriented, may be placed between the light pipe illuminator 14 and the detector array 26. They can cover the entire detector array 26, or only part of it. They can also be used in conjunction with filters, for example color filters 18a, already built into the detector array 26. Using the polarization filters, the first subset of detectors can detect a first polarization component of the response radiation 19 and the second subset of detectors can detect a second polarization component of the response radiation 19, the second polarization component being orthogonal to the first polarization component. Other permutations and combinations will be apparent to one skilled in the art.

From the foregoing, it will be appreciated that the present invention is novel and offers advantages over the current art. The present invention results in a more effective technique and apparatus for biochemical analysis. Although a specific embodiment of the invention is described and illustrated above, the invention is not to be limited to the specific forms or arrangements of parts so described and illustrated. For example, differing configurations, sizes, or materials may be used to practice the present invention. The invention is limited by the claims that follow.

What is claimed is:

1. An apparatus comprising
a radiation source for generating stimulus radiation;
a sensor array including an array of sensors;
a light pipe illuminator adapted to direct the stimulus radiation from said radiation source to said sensor array;
wherein each sensor of said sensor array having fluorophore for generating response radiation in response to the stimulus radiation when analyte is present within the sensor;
a detector array for detecting the response radiation, the detector array including a plurality of detectors grouped in sets, each set associated with a single sensor; and
wherein said light pipe illuminator is positioned between said sensor array and said detector array.

2. The apparatus recited in claim 1 wherein the detector array is a CMOS imaging array.

3. The apparatus recited in claim 1 further comprising a detector unit including the detector array, the detector unit converting the response radiation to digital values.

4. The apparatus recited in claim 3 further comprising a processor for analyzing the digital values.

5. The apparatus recited in claim 1 wherein a first set of detectors includes a first subset of detectors suitable for detecting radiation within a first range of wavelengths, a second subset of detectors suitable for detecting radiation within second range of wavelengths, and a third subset of detectors suitable for detecting radiation within third range of wavelengths.

6. The apparatus recited in claim 1 further comprising a detector unit having said detector array, the detector unit further comprising additional circuitry for providing digital values representing the response radiation from the sensor.

7. The apparatus recited in claim 6 further comprising a processor for analyzing the digitized values.

8. The apparatus recited in claim 1 wherein a set of detectors include a first subset of detectors suitable for detecting a first polarization component of the response radiation and a second subset of detectors suitable for detecting a second polarization component of the response radiation, the second polarization component being orthogonal to the first polarized component.

9. The apparatus recited in claim 1 wherein at least one sensor includes at least two fluorophores such that when stimulated, the sample generates the response radiation in several color bands.

10. The apparatus recited in claim 9 wherein a set of detectors includes a first subset for detecting a first color band and a second subset for detecting a second color band.

11. The apparatus recited in claim 1 wherein the at least one sensor includes a reference fluorophore.

12. The apparatus recited in claim 1 whereby the response radiation passes through said light pipe illuminator before impinging on said detector.

* * * * *